(12) United States Patent
Kermani et al.

(10) Patent No.: US 11,527,305 B2
(45) Date of Patent: Dec. 13, 2022

(54) MACHINE LEARNING FOR SOMATIC SINGLE NUCLEOTIDE VARIANT DETECTION IN CELL-FREE TUMOR NUCLEIC ACID SEQUENCING APPLICATIONS

(71) Applicant: GUARDANT HEALTH, INC., Redwood City, CA (US)

(72) Inventors: Bahram Ghaffarzadeh Kermani, Los Altos, CA (US); Helmy Eltoukhy, Atherton, CA (US)

(73) Assignee: Guardant Health, Inc., Palo Alto, CA (US)

( * ) Notice: Subject to any disclaimer, the term of this patent is extended or adjusted under 35 U.S.C. 154(b) by 0 days.

(21) Appl. No.: 17/178,102

(22) Filed: Feb. 17, 2021

(65) Prior Publication Data

US 2021/0265013 A1    Aug. 26, 2021

Related U.S. Application Data

(63) Continuation of application No. 15/255,028, filed on Sep. 1, 2016, now Pat. No. 11,302,416.
(Continued)

(51) Int. Cl.
*G16B 20/20* (2019.01)
*G16B 30/00* (2019.01)
(Continued)

(52) U.S. Cl.
CPC ............ *G16B 20/20* (2019.02); *G16B 30/00* (2019.02); *G16B 35/00* (2019.02); *G16B 40/00* (2019.02); *G16B 40/20* (2019.02); *G16C 20/60* (2019.02)

(58) Field of Classification Search
CPC ........ G16B 30/00; G16B 20/00; G16B 30/10; G16B 40/00; G16B 20/20; G16B 40/20;
(Continued)

(56) References Cited

U.S. PATENT DOCUMENTS 10,704,086 B2 *  7/2020  Talasaz ................ C12Q 1/6827
10,894,974 B2 *  1/2021  Talasaz .................. G16B 30/10
(Continued)

FOREIGN PATENT DOCUMENTS

AU    2015249846 A1 *  11/2016  ............. G06F 19/00
WO    2014039556 A1    3/2014
(Continued)

OTHER PUBLICATIONS

Manning, T. Biologically inspired intelligent decision making. (2014) Bioengineered 5:2 p. 80-95. (published online Dec. 16, 2013) (Year: 2014).*
(Continued)

*Primary Examiner* — Mary K Zeman
(74) *Attorney, Agent, or Firm* — Timothy A. Hott

(57) ABSTRACT

Systems and methods are disclosed to detect single-nucleotide variations (SNVs) from somatic sources in a cell-free biological sample of a subject by generating training data with class labels; in computer memory, generating a machine learning unit comprising one output for each of adenine (A), cytosine (C), guanine (G), and thymine (T) calls; training the machine learning unit; and applying the machine learning unit to detect the SNVs from somatic sources in the cell-free biological sample of the subject, wherein the cell-free biological sample comprises a mixture of nucleic acid molecules from somatic and germline sources.

20 Claims, 4 Drawing Sheets

Related U.S. Application Data

(60) Provisional application No. 62/213,448, filed on Sep. 2, 2015.

(51) Int. Cl.
*G16B 35/00* (2019.01)
*G16B 40/00* (2019.01)
*G16C 20/60* (2019.01)
*G16B 40/20* (2019.01)

(58) Field of Classification Search
CPC ........ G16B 30/20; G16B 15/00; G16B 40/30; G16B 5/20; G16B 5/00; G16B 50/00; G16B 20/40; G16B 50/30; G16B 45/00; G16B 35/00; G16B 35/20; G16B 50/20; G12Q 1/6869; G12Q 1/6886; G12Q 2600/156; G12Q 1/6827; G12Q 1/6883; G12Q 2600/118; G12Q 2537/165; G16H 50/20; G16H 10/40; G16H 50/30; G16H 50/70; G16H 10/60; G16H 70/60; G16H 50/50; G06N 20/00; G06N 7/005; G06N 20/20; G06N 5/003; G06N 20/10; G06N 3/0454; G06N 3/08; G06N 3/084; G06N 5/04; G06N 3/006; G06N 3/088; G06N 3/04; G06N 3/0445; G06N 3/0481; G06N 3/082; G06N 5/047; G06N 5/02; G06N 5/022; G06N 7/023; G06F 19/00; G06F 17/10; G06F 17/18; G06F 16/285; G06F 30/27; G06F 16/2465; G06F 19/34; G06F 2216/03; G06K 9/6267; G06K 9/6231; G06K 9/6232; G06K 9/6256; G06K 9/6271

See application file for complete search history.

(56) References Cited

U.S. PATENT DOCUMENTS

| | | |
|---|---|---|
| 11,302,416 B2 | 4/2022 | Kermani et al. |
| 2013/0130923 A1 | 5/2013 | Ehrich et al. |
| 2017/0061072 A1 | 3/2017 | Kermani et al. |
| 2018/0251848 A1 | 9/2018 | Diehn et al. |

FOREIGN PATENT DOCUMENTS

| | | | |
|---|---|---|---|
| WO | 2014149134 A2 | 9/2014 | |
| WO | WO-2016183106 A1 * | 11/2016 | ........... C12Q 1/6886 |

OTHER PUBLICATIONS

Stokes, M. E. Novel extensions of label propagation for biomarker discovery in genomic data. Dissertation, University of Pittsburgh, 2014. 134 pages. (Year: 2014).*

Agarwal, A. et al. "Commercial landscape of noninvasive prenatal testing in the United States" Prenatal Diagnosis (2013) 33:521-531.

Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.

Manning, T. et al. "Biologically inspired intelligent decision making" Bioengineered (2013) 5(2):80-95.

Newman, et al. An ultrasensitive method for quantitating circulating tumor DNA with broad patient coverage Nat Med. May 2014;20(5):548-54. doi: 10.1038/nm.3519. Epub Apr. 6, 2014.

Paweleiz, C.P. et al. "Bias-corrected targeted next-generation sequencing for rapid, multiplexed detection of actionable alterations in cell-free DNA from advanced lung cancer patients" Clin Canc Res (2016) 22(4):915-922.

Phallen, J. et al. "Direct detection of early-stage cancers using circulating tumor DNA" Sci Trans Med (2017) vol. 9, Issue 403, eaan2415DOI: 10.1126/scitranslmed.aan2415.

Stokes, M.E. "Novel extensions of label propagation for biomarker discovery in genomic data" Dissertation, University of Pittsburgh (2014) 134 pages.

Final Office Action for U.S. Appl. No. 15/255,028, dated Dec. 5, 2019.

Final Office Action for U.S. Appl. No. 15/255,028, dated Mar. 3, 2021.

Office Action for U.S. Appl. No. 15/255,028, dated Mar. 21, 2019.
Office Action for U.S. Appl. No. 15/255,028, dated Jul. 15, 2020.
Office Action for U.S. Appl. No. 15/255,028, dated Jun. 28, 2021.

* cited by examiner

| |
|---|
| Generate training data with class labels (1) |
| Determine germline genotypes (2) |
| Use Variant Base to emulate somatic change (3) |
| Generate training examples from permutation of each pair of normals (4) |
| Generate machine learning unit such as a supervised learning machine, an SVM, a 3-output or 4-output neural network (one output for each of A, C, G, and T calls) (5) |
| Determine machine learning data structure (6) considering one or more input features:<br>    biological significance in SNV detection,<br>    tally vectors for each of the training set vectors,<br>    statistics of a series of normal samples at the base position of interest, or<br>    items (binary or real-valued) that represent existence or the probability of disturbance caused by a repeat structure at the base position of interest |
| Train the machine learning unit (7) |
| Apply the machine learning unit to detect the SNVs from somatic sources in the cell-free biological sample of the subject, wherein the cell-free biological sample comprises a mixture of nucleic acid molecules from somatic and germline sources |

FIG. 1

| Mixture | Class Labels ||||| Counts |||||||||||||
| | Locus 1 | Locus 2 | ... | Locus 1000 | | Locus 1 |||| Locus 2 |||| ... | Locus 1000 ||||
| | | | | | | A | T | G | C | A | T | G | C | | A | T | G | C |
|---|---|---|---|---|---|---|---|---|---|---|---|---|---|---|---|---|---|---|
| 1 | C | Ref. | | T | | 988 | 1 | 0 | 11 | 0 | 999 | 1 | 0 | | 0 | 11 | 988 | 1 |
| 2 | Ref. | A | | Ref. | | 999 | 0 | 1 | 0 | 1 | 988 | 0 | 1 | | 1 | 0 | 999 | 0 |
| 3 | C | Ref. | | T | | 985 | 2 | 1 | 12 | 1 | 999 | 0 | 0 | | 1 | 12 | 985 | 2 |
| 4 | Ref. | A | | Ref. | | 999 | 1 | 0 | 0 | 12 | 985 | 1 | 2 | | 0 | 1 | 999 | 0 |
| ... | | | | | | | | | | | | | | | | | | |
| 97 | Ref. | G | | Ref. | | 999 | 1 | 0 | 0 | 0 | 989 | 10 | 1 | | 0 | 1 | 999 | 0 |
| 98 | Ref. | Ref. | | A | | 998 | 0 | 1 | 1 | 1 | 998 | 1 | 0 | | 10 | 2 | 987 | 1 |
| 99 | C | A | | T | | 987 | 2 | 1 | 10 | 10 | 987 | 1 | 2 | | 0 | 9 | 990 | 1 |
| 100 | G | Ref. | | Ref. | | 990 | 0 | 9 | 1 | 0 | 998 | 1 | 1 | | 1 | 0 | 998 | 1 |

FIG. 4

MACHINE LEARNING FOR SOMATIC SINGLE NUCLEOTIDE VARIANT DETECTION IN CELL-FREE TUMOR NUCLEIC ACID SEQUENCING APPLICATIONS

CROSS-REFERENCE

This application is a continuation of U.S. patent application Ser. No. 15/255,028, filed Sep. 1, 2016, which application claims priority to U.S. Provisional Patent Application No. 62/213,448, filed Sep. 2, 2015, which applications are entirely incorporated herein by reference.

BACKGROUND

Single-nucleotide variation (SNV) detection is a critical step in a typical analysis pipeline for re-sequencing applications. It refers to the detection (or determination) of single-base differences between a newly generated sequence and a reference sequence. Besides SNVs, there are other common types of variations between an individual sample's sequence and a reference sequence. Examples of such variations are: (1) indels (e.g., insertions or deletions), (2) copy number variations (CNVs), which may include changes involving very long stretches (e.g., thousands or even millions of nucleotides), and (3) chromosomal rearrangements, such as gene fusions. Conventionally an indel (or Indel, InDel) is understood as either an insertion or a deletion at a given location, with the plural form indels (or Indels, InDels). Although the detection of these two latter types of variants is generally more difficult than the detection of SNVs, the present disclosure may be applied to these variations also, as will be clear to those skilled in the relevant art.

Variant detection, including SNV detection, indel detection, and SV or CNV detection, follows a mapping or alignment step in the analysis pipeline. Mapping or alignment refers to the operation by which the original sequencing reads are mapped to the reference sequence. Because the sequencing reads are short, and there are many repeated regions in the very long reference sequence (e.g., the human reference genome is ~3 billion nucleotides long), finding the precise position in the reference sequence where a read is mapped to is also challenging. Genome mapping methods, which are known to those skilled in the art, are not discussed here.

One reason SNV detection is difficult when using next-generation sequencing (NGS) approaches is because the error rate produced by conventional NGS technologies (e.g., Illumina technology) is commonly believed to be on the level of 0.1% to 1%, which is zero to one order of magnitude higher than the SNV rate (that is, the proportion of nucleotides that are different between any two individuals, or between one's genome and the reference genome, e.g., ~0.1%). Both SNVs and sequencing errors are reflected as differences between the sequencing data and the reference sequence. In other words, the "noise" (e.g., sequencing error) could be as high as one order of magnitude higher than the "signal" (e.g., real SNVs).

SUMMARY

The present disclosure provides methods and systems for detection of single-nucleotide variations (SNVs) from somatic sources in a cell-free biological sample of a subject, such as in a mixture of nucleic acid molecules from somatic and germline sources.

Systems and methods are disclosed to detect single-nucleotide variations (SNVs) from somatic sources in a cell-free biological sample of a subject by generating training data with class labels; forming a machine learning unit having one output for each of adenine (A), cytosine (C), guanine (G), and thymine (T) base calls, respectively; training the machine learning unit with a training set of biological samples; and applying the machine learning unit to detect the SNVs from somatic sources in the cell-free biological sample, wherein the cell-free biological sample may comprise a mixture of nucleic acid molecules (e.g., deoxyribonucleic acid (DNA)) from somatic and germline sources, e.g., cells comprising somatic mutations and germline DNA.

Advantages of the system may include one or more of the following. The system can handle a large number of input features used for performing the SNV detections. For instance, the GC content information (which is very informative) can be utilized. The system can be highly scalable. The system does not necessarily rely on hard thresholds on the number of molecules which helps in scaling with a variable coverage. The system can make accurate calls even when deviations from nominal value (higher or lower). The system provides SNV detection optimality—in comparison, there is no guarantee that heuristic methods will result in the optimal detection. The system provides probabilistic quantification with a quality score that can be globally used in a downstream probabilistic (e.g., Bayesian) method.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 shows an exemplary process to perform detection of single-nucleotide variations (SNVs) from somatic sources in a cell-free biological sample of a subject, wherein the cell-free biological sample comprises a mixture of nucleic acid molecules from somatic and germline sources.

FIG. 4 shows an exemplary training data set.

DETAILED DESCRIPTION

Figure 2A:
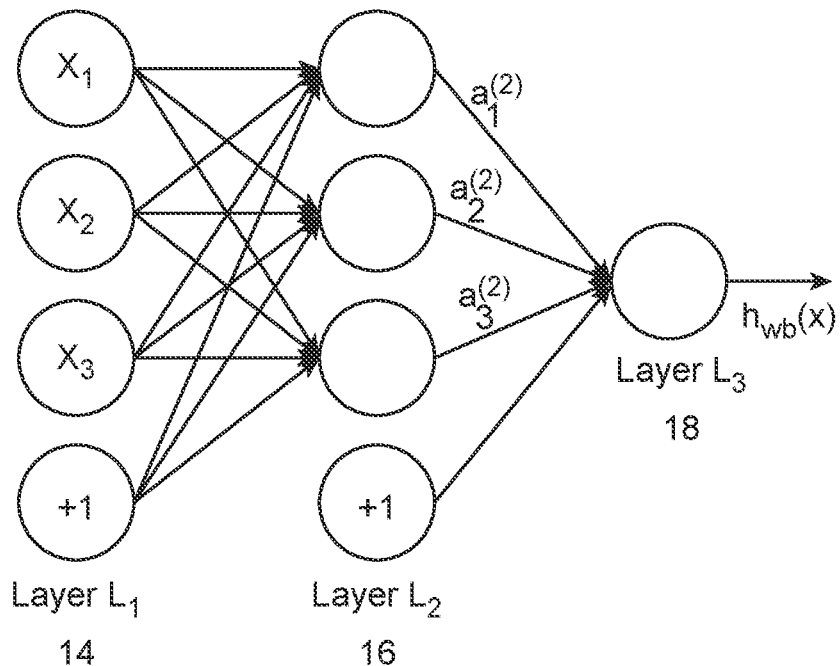
FIG. 2A and FIG. 2B show an exemplary learning machine unit such as a three-output or four-output neural network.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Cell-free deoxyribonucleic acid (DNA) from a subject with cancer typically will be a mixture of germline DNA and cancer cell DNA, which contains somatic mutations (hereinafter, "somatic DNA"). When such a mixture is sequenced, base calls at a genomic base position (hereinafter, "base position") among sequence reads in which the cancer cells have a somatic mutation will be a combination of calls from the germline DNA and calls from the somatic DNA. In addition, there is chance of sequencing errors. So, for example, 1,000 reads from a cancer patient may produce calls of A=988, T=2, G=1, and C=9. In such a case, a user might call the presence of C at the genomic base position in the sample, and might call it at ~1%. In this way, for each of a plurality of genomic base positions in a sample, the presence of one or more bases at the genomic base position, the relative frequency of one or more bases at the genomic base position, and/or the probability of the presence of each of one or more bases at the genomic base position can all be determined, or called.

Machine learning methods can be used to generate models that call the presence of a base at a genomic base position in a sample comprising mixed DNA (e.g., germline DNA and somatic DNA) with higher accuracy than a heuristic method, and, optionally, providing a confidence level of the call. Such models can be generated by providing a machine learning unit with training data in which the expected output is known in advance, e.g. an output in which it is known that 99% of the bases at a genomic base position are A and 1% are C.

Such a training set can be provided as follows. Cell-free DNA from a plurality of presumably homogenous normal samples may be sequenced. These samples can be, for example, cell-free DNA from individuals who do not have a condition in which diseased cells comprise somatic mutations, e.g., healthy individuals or non-cancer individuals. This provides a set of sequences in which the base at each genomic base position examined is expected to be the same for all molecules in the sample that are homozygous at that corresponding locus. This can produce, for each sample, a vector indicating, at each genomic base position, the counts of each base at the genomic base position.

The polymorphism rate in the human population is about 0.1% at any genomic base position. Therefore, in any one sample, 0.1% of the base positions are expected to harbor variants, or, in a panel of 160,000 bases, about 160 variants per sample. Put another way, in a set of 1,000 samples, in the worst case, at any particular base position, one might expect to find a single-nucleotide polymorphism (SNP) in about one of the samples.

At this point, the method can proceed with an in vitro approach or an in silico approach. Both approaches involve generating reads from mixtures of samples.

In an in vitro approach, a collection of samples comprising homogenous DNA, e.g., only germline DNA, is provided. The DNA is sequenced to determine genotype at each base position of interest. DNA from the samples is then mixed to provide mixed samples having known relative proportions of DNA from each sample in the mixture. Suppose, for example, one is provided with a set of 100 samples: a1, a2, a3, . . . , a100. A set of mixtures can be produced in which each sample is mixed with each other sample at a ratio of, for example, 99% to 1%. In one example, this can produce a set of 9,900 mixtures with composition as follows: 99% a1×1% a2, 99% a1×1% a3, 99% a1×1% a4, . . . , 99% a1×1% a99, 99% a1×1% a100. Other mixture sets can also be provided. For example, a mixture set could be 99% a100×1% a99, 99% a100×1% a98, 99% a100×1% a97, . . . , 99% a100×1% a2, 99% a100×1% a1. In another example, the percentages can vary, for example, 95% a1×5% a2, 95% a1×5% a3, 95% a1×5% a4, . . . , 95% a1×5% a99, 95% a1×5% a100 (as shown in FIG. 4).

For each of these mixtures, the expected output in terms of base calls at each base position is known. For example, if it is known that at a particular base position, sample a1 has A (which may be the base in the reference genome) and sample a2 has C, the expected output of sequencing the mixture 99% a1×1% a2 is, for 1,000 reads, for A-T-G-C, [990-0-0-10].

A "class label" can be applied to each sample indicating the classification of the sample for any number of input features. For example, the class labels for the set of mixtures above could indicate the identity of variants at various base positions (e.g., "C" in the mixture 99% a1×1% a2, to indicate the sample has the presence of C at a particular base position).

All the mixtures are sequenced, producing a vector including data indicating, for each mixture, the read or molecule count (or %) of each base at each base position tested in each mixture. Other features of the sample can be included in the vector for each mixture, such as GC content at a base position, entropy, detection of reads from both or only one strand, etc. This constitutes the training set.

In an in silico approach, each sample is sequenced to produce sets of sequence reads. "Mixtures" are produced by, for example, combining reads from different samples in prescribed percentages. For example, mixture 99% a1×1% a2, could include 990 reads from sample a1 and 10 reads from sample a2. Ideally, these reads are randomly selected. The training set comprises tally vectors from each in silico mixture, in addition to other selected features. Again, there is an "expected" output for each mixture, and each mixture may be provided with one or more class labels for any number of input features.

The resulting training sets are provided to a machine learning unit, such as a neural network or a support vector machine. Using the training set, the machine learning unit may generate a model to classify the sample according to base identity at one or more base positions. This is also referred to as "calling" a base. The model developed may employ information from any part of a test vector. That is, it may use not only information about tally vectors from the base position in question, but tally vectors from other base positions proximal or distal to the test base position or non-sequence read information included as a feature of the vector.

FIG. 1 shows an exemplary process to perform detection of single-nucleotide variations (SNVs) from somatic sources, in a mixture of somatic and germline cell-free DNA data. The process may use a multi-layer-perceptron (MLP) neural network shown in FIG. 2 as a machine learning method. However, it must be noted that other machine learning methods such as support-vector machines (SVMs), other neural networks (e.g., RBNN), neuro-fuzzy, and other methods could also be utilized.

Turning now to FIG. 1, an exemplary process is disclosed for detecting SNVs from somatic sources. The SNV calls are made from mixtures of nucleic acid molecules from somatic and germline sources using the process that:

Generates training data with class labels (1)
Determines germline and somatic genotypes (2)
Uses Variant Base to emulate somatic change (3)
Generates training examples from permutation of each pair of normals (4)
Generates a machine learning unit such as a supervised learning machine, a SVM, 3 output or 4-output neural network (one output for each of A, C, G, and T calls) (5)
Generates machine learning data structure (6) considering input features:
  biological significance in SNV detection,
  tally vectors for each of the training set vectors, or
  statistics of a series of normals samples at the base position of interest
  items (binary or real-valued) that represent existence or the probability of disturbance caused by a repeat structure at the base position of interest
Trains the learning unit (7)
Applies the learning unit to detect the SNVs from somatic sources in the cell-free biological sample of the subject, wherein the cell-free biological sample comprises a mixture of somatic and germline sources (8)

Each of the foregoing steps is detailed next.

In step 1, to enable a supervised learning, a series of training data along with class labels are needed. In an embodiment, the training set could be an in silico mixture of one normal cell-free DNA sample in another normal cell-free DNA sample. The mixture can be formulated as $a1*x1+a2*x2$, where $a1$ and $a2$ are the mixture coefficients, and $a1+a2=1$, and where $x1$ and $x2$ are the first and second normal set, respectively. In this embodiment, $a1$ is much larger than $a2$. For example, if $a1=0.99$ and $a2=0.01$, 1% of $x2$ is mixed with 99% of $x1$. Therefore, this scenario could illustrate a case of 1% somatic in 99% germline background.

In step 2, the genotypes of x1 (emulating germline) and x2 (emulating somatic) are found, independently using their pure (pre-mix) data. This can be done via various genotype calling algorithms.

For example, in a genotyping analysis, DNA from a population of several individuals can be analyzed by a set of multiplexed arrays. The data for each multiplexed array may be self-normalized using the information contained in that specific array. This normalization algorithm may adjust for nominal intensity variations observed in the two color channels, background differences between the channels, and possible crosstalk between the dyes. The behavior of each base position may then be modeled using a clustering algorithm that incorporates several biological heuristics on SNP genotyping. In cases where fewer than three clusters are observed (e.g., due to low minor-allele frequency), locations and shapes of the missing clusters may be estimated using neural networks. Depending on the shapes of the clusters and their relative distance to each other, a statistical score may be devised (a Training score). A score such as GenCall Score is designed to mimic evaluations made by a human expert's visual and cognitive systems. In addition, it has been evolved using the genotyping data from top and bottom strands. This score may be combined with several penalty terms (e.g., low intensity, mismatch between existing and predicted clusters) in order to make up the Training score. The Training score, along with the cluster positions and shapes for each SNP, is saved for use by the calling algorithm.

To call genotypes for an individual's DNA, the calling algorithm may take the DNA's intensity values and the information generated by the clustering algorithm; subsequently, it may then identify to which cluster the data for any specific base position (of the DNA of interest) corresponds. The DNA data may first be normalized (using the same procedure as for the clustering algorithm). The calling operation (classification) may be performed using a Bayesian model. The score for each call's Call Score is the product of the Training Score and a data-to-model fit score. After scoring all the base positions in the DNA of interest, the application may compute a composite score for that DNA (DNA Score). Subsequently, the Call score of each base position for this DNA may be further penalized by the DNA Score. The Call Score may not be a probability, but a score, which may be designed to rank and filter out failed genotypes, DNAs, and/or base positions. Call Scores may be averaged among DNAs and among base positions for purposes of evaluating the quality of the genotyping within a particular DNA or base position. Using GC10 and GC50 Scores, a user may choose to fail particularly poor performing base positions, for instance, by discarding base positions with GC10 of 0.1 or lower. Also, a series of aggregate statistics (i.e., average) of the GC10 or GC50 scores for each DNA may be used to identify low-quality DNAs (for instance, a user may discard DNA samples with average GC10 scores of 0.2 or lower).

In step 3, reference bases (i.e., the bases that get similar calls between x1 and x2) are relatively uninformative. The homozygous and heterozygous calls, however, may be informative. For instance, in a case where x1 is a reference base (e.g., A) and x2 is a variant base (e.g., C), the variant could emulate a somatic change. For instance, suppose the following tally vectors (counts of A, C, G, and T at a particular base position) are available for x1 and x2, respectively: [1000 0 1 2] and [1 1000 3 1]. The mixture tally vector $(0.99 \times x1 + 0.01 \times x2)$ could resemble the following: [999 10 2 2] (note the stochastic changes in the small values). In this case, A=999 could represent the germline contribution and C=10 could represent the somatic contribution in the mixture. Since in an embodiment, an objective may be to find the somatic contribution, C would be the class label with the molecular support of 10.

In step 4, if there are N normals, the permutation of each pair of normals could be used to render a series of training examples (as detailed above). For N normals, there would be $N*(N-1)$ permutations. If $N \gg 1$, then this number can be approximated by $N^2$. Assuming a panel has M bases, and the rate of polymorphism is 0.1%, there would be M/1000 examples from each pair. Therefore, the total number of examples available for training is $T=N*(N-1)*M/1000$. For N=30 and M=168,000, T is about 150,000 training patterns for training a classifier. However, this number may be filtered/reduced for various reasons, e.g, excluding heterozygotes or excluding calls with insufficient support. Nevertheless, a number of T of about 100,000 may be easily attainable.

In general, training data sets can be generated from training samples. These training samples are generated by: (a) preparing a plurality of mixtures, wherein each mixture comprises a first normal cell-free DNA sample in a second normal cell-free DNA sample; and (b) sequencing the cell-free DNA in each mixture of the plurality of mixtures of cell-free DNA. A set of mixtures may be prepared, said mixture comprising a permutation of substantially each pair or first and second normal cell-free DNA samples. Each mixture may comprise various relative concentrations of the first and second normal cell-free DNA samples, e.g., 1% and 99%, 2% and 98%, 3% and 97%, 4% and 96%, 5% and 95%, 6% and 94%, 7% and 93%, 8% and 92%, 9% and 91%, 10% and 90%, 15% and 85%, 20% and 80%, 25% and 75%, 30% and 70%, 35% and 65%, 40% and 60%, 45% and 55%, or 50% and 50%, respectively. Collectively, this set of training examples may be used to generate a training data set to train a machine learning unit.

In step 5, a three-output or four-output neural network (one output for each of A, C, G, and T calls) can be devised. These outputs, given sigmoidal neurons of the type logsig in their neurons, will render values in the range [0, 1], From a theoretical perspective, it is known that if an MLP neural network is trained properly, such outputs should converge to the actual probability values. Note that each of A, C, G, and T can take values in the range [0, 1]; and therefore, the caller is indeed a possiblistic caller, which is advantageous to methods of probabilistic calls. This is due to the fact that the A, C, G and T outputs are not forced to sum to 1. This means that a multi-call could be made (for instance, the call could be both A and G), which could be alluding to a heterogeneous tumor source (i.e., each tumor causing a different variant). In addition to each of the outputs generating a single score, the neural network may further combine all outputs into a single SNV detection.

In step 6, the inputs of the neural network comprise input features that have biological significance in the somatic call (e.g., SNV detection) (or need to be removed from the germline contribution). Since somatic calls (e.g., SNV detection) are based on coverage data mapped to a reference genome, any factor contributing to a change in the coverage of the data could be considered as a useful input feature. An example of such a feature is the GC-content. It is well known that GC-content is one of the strong contextual influencers of the coverage data in NGS. Often times, such relationship is removed via inverse functions, which are subject to amplifying noise, particularly in the areas of the curve that the slope is low (which results in high slopes in the inverse function). In this invention, the GC-content could be corrected by the implicit relationship that the machine learning unit (e.g. neural network) would find. In addition to the GC-content, other contextual information (many of which, unlike GC-content, do not have a direct and tangible correlation with coverage) could be used, e.g., the entropy of one or more bases proximal to the base position of interest (in a certain radius).

In alternative 6B, other inputs of the neural network could include the actual tally vectors for each of the training set vectors. For example, the counts of A, C, G, and T at a certain base position could be considered as inputs. These counts can also be broken down to various components, for instance each of the A, C, G, and T based could be decomposed into sub-count components, including single molecule support, more than 1 molecule support, Watson/Crick support, etc. Since an objective is to make somatic calls, as an alternative embodiment, the base with the highest tally number (believed to be from germline source) can be eliminated from the input set. For instance, if the count for A is 999, then only C, G, and T could be input to the neural network and A could be eliminated.

In alternative 6C, to reduce noise, statistics of a series of normal samples at the base position of interest could also be considered as inputs. For instance, mean and standard deviation (or median and interquartile range (IQR)) of the normals for each of the A, C, G, T bases, or for the combination of the bases (sum of A, C, G, T) could be considered as other inputs.

In alternative 6D, other inputs could include features (binary or real-valued) that represent existence or the probability of disturbance caused by a repeat structure at the base position of interest. Examples of such repeats include SINEs (in particular ALUs) and LINEs in the genome.

Artificial neural networks (NNets) mimic networks of "neurons" based on the neural structure of the brain. They process records one at a time, or in a batch mode, and "learn" by comparing their classification of the record (which, at the outset, is largely arbitrary) with the known actual classification of the record. In MLP-NNets, the errors from the initial classification of the first record is fed back into the network, and are used to modify the network's algorithm the second time around, and so on for many iterations.

FIG. 2A shows an exemplary MLP with input layer neurons 14, hidden layer neurons 16, and output layer neurons 18. A minimum of one hidden layer is recommended if the neural network is to learn a general pattern. This layer could be linear or sigmoidal. More layers could also be considered.

Figure 2B:
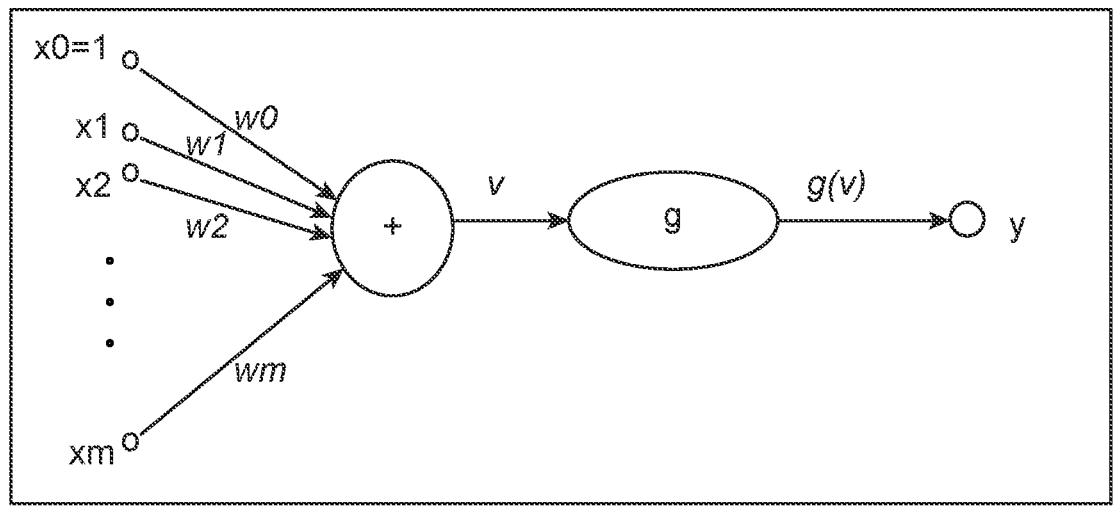

Turning now to step 7, the process trains the neural network. As shown in FIG. 2B, a neuron in an artificial neural network is a set of input values (xi) and associated weights (wi) and a function (g) that sums the weights and maps the results to an output (y). A bias (constant term) is also provided to each neuron. Neurons are organized into layers. The input layer is composed not of full neurons, but rather consists simply of the values in a data record, that constitute inputs to the next layer of neurons. The next layer is called a hidden layer; there may be several hidden layers. The final layer is the output layer, where, in some cases, there may be one node for each class. A single sweep forward through the network results in the assignment of a value to each output node, and the record is assigned to whichever class's node had the highest value.

In the training phase, the correct class for each record is known (this is termed supervised training), and the output nodes can therefore be assigned "correct" values—"1" for the node corresponding to the correct class, and "0" for the others. (In practice, it has been found better to use values of 0.9 and 0.1, respectively.) It is thus possible to compare the network's calculated values for the output nodes to these "correct" values, and to calculate an error term for each node (the "Delta" rule). These error terms are then used to adjust the weights in the hidden layers so that, ideally, at each successive iteration, the output values will be closer to, and eventually converge to, the "correct" values.

The neural networks uses an iterative learning process in which data cases (rows) are presented to the network one at a time, and the weights associated with the input values are adjusted each time.

After all cases are presented, the process often starts over again. During this learning phase, the network learns by adjusting the weights so as to be able to predict the correct class label of input samples. Neural network learning is also referred to as "connectionist learning," due to connections between the units. Advantages of neural networks include their high tolerance to noisy data, as well as their ability to classify patterns on which they have not been trained. One neural network algorithm is back-propagation algorithm, such as Levenberg-Marquadt. Once a network has been structured for a particular application, that network is ready to be trained. To start this process, the initial weights are chosen randomly. Then the training, or learning, begins.

The network processes the records in the training data one at a time, using the weights and functions in the hidden layers, then compares the resulting outputs against the desired outputs. Errors are then propagated back through the system, causing the system to adjust the weights for application to the next record to be processed. This process occurs over and over as the weights are continually tweaked. During the training of a network the same set of data is processed many times as the connection weights are continually refined.

In an embodiment with Feedforward, Back-Propagation neural networks, the training process uses some variant of the Delta Rule, which starts with the calculated difference between the actual outputs and the desired outputs. Using this error, connection weights are increased in proportion to the error times a scaling factor for global accuracy. Doing this for an individual node means that the inputs, the output, and the desired output all have to be present at the same processing element. The system determines which input contributed the most to an incorrect output and how does that element get changed to correct the error. An inactive node would not contribute to the error and would have no need to change its weights. To solve this problem, training inputs are applied to the input layer of the network, and desired outputs are compared at the output layer. During the learning process, a forward sweep is made through the network, and the output of each element is computed layer by layer. The difference between the output of the final layer and the desired output is back-propagated to the previous layer(s), usually modified by the derivative of the transfer function, and the connection weights are normally adjusted using the Delta Rule. This process proceeds for the previous layer(s) until the input layer is reached.

Finally, the process applies the neural network to perform detection of SNVs from somatic sources, in a mixture of somatic and germline cell-free DNA data (8). This can be done by applying the input values in a feed-forward manner through the neural network to arrive at the SNV detections.

In an embodiment, the training step of the machine learning unit on the training data set may generate one or more classification models for applying to a test sample. These classification models may be applied to a test sample to (1) detect the presence of a base at each of a plurality of genomic base positions in a test sample, (2) to call a relative frequency of each of one or more bases at each of a plurality of genomic base positions in the test sample, and/or (3) to call a probability of the presence of each of one or more bases at each of a plurality of genomic base positions in the test sample.

Figure 3:
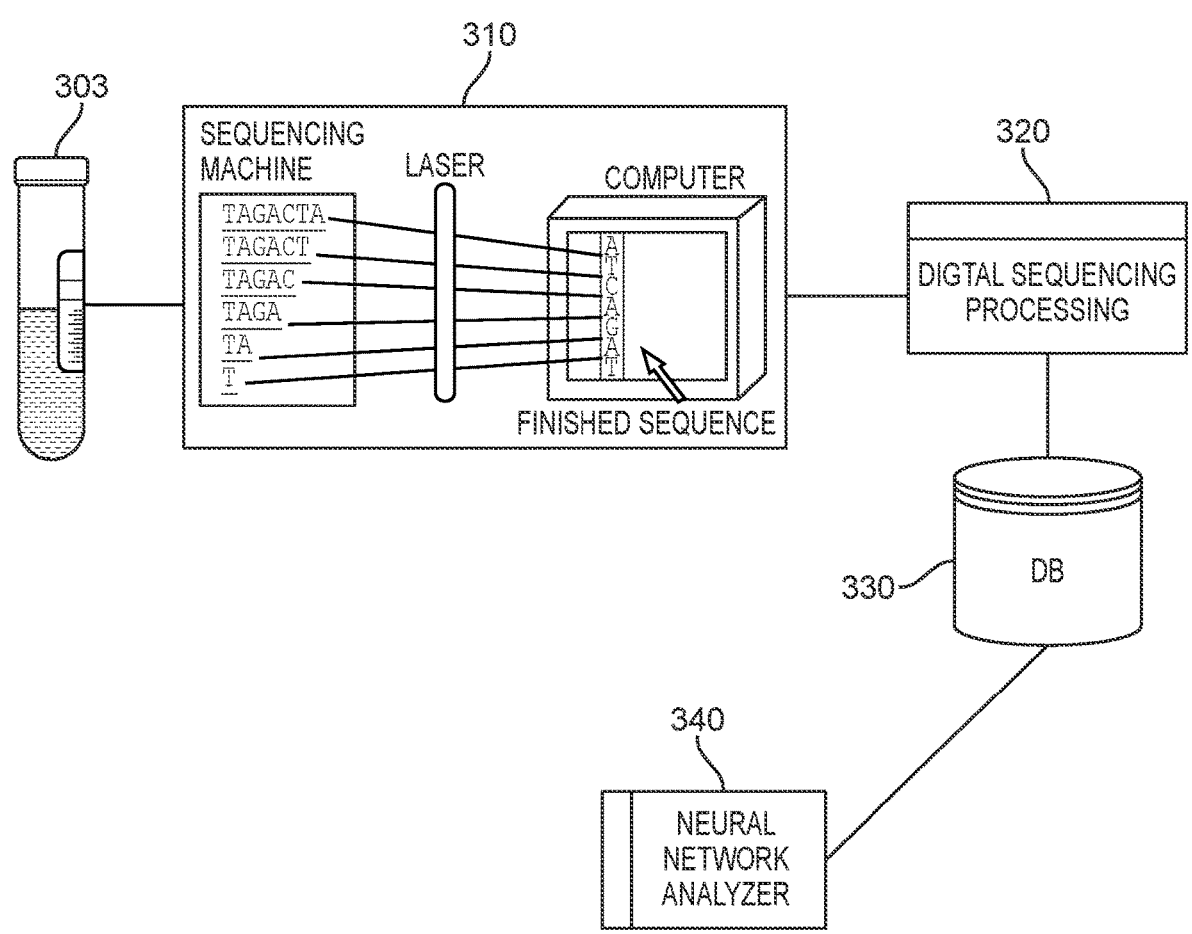
FIG. 3 shows an exemplary digital sequencing system with the machine learning unit for SNV detection.

Referring to FIG. 3, an illustrative embodiment of a digital sequencer and neural network system is shown and is designated. The system receives blood samples 303 from patients with cancer, among other diseases. Cancer tumors continually shed their unique genomic material the root cause of most cancers—into the bloodstream. As the telltale genomic "signals" are so weak, next-generation sequencers can only detect such signals sporadically or in patients with terminally high tumor burden. Such error rates and bias can be orders of magnitude higher than what is required to reliably detect de novo genomic alterations associated with cancer. To address this issue, a digital sequencer 310 is used. The digital sequencer may be a nucleic acid sequencer, such as a DNA sequencer. The DNA sequencer may be a scientific instrument used to automate the DNA sequencing process. Given a sample of DNA, a DNA sequencer is used to determine the order of the four bases: adenine (A), guanine (G), cytosine (C), and thymine (T). The order of the DNA bases may be reported as a text string, called a read. Some DNA signals may originate from fluorochromes attached to nucleotides. In an embodiment, the four bases (and corresponding input parameters of the machine learning unit) may be adenine (A), guanine (G), cytosine (C), and uracil (U), corresponding to ribonucleic acid (RNA) sequencing.

In an embodiment, digital sequencers from Guardant Health can be used, which reduces the noise and distortion generated by next-generation sequencing to almost zero. The output of sequencer 310 is digitally processed in unit 320 and stored in a data center with database(s) 330. While 310 illustrates a Sanger sequencing machine, other sequencers such as Illumina HiSeq2500 can be used. Also, the DB 330 is not necessary as the data from unit 320 can flow directly to a deep analyzer 340. The deep analyzer 340 can retrieve information from the database 330 and run high-level information with biomedical meanings from all available data, e.g., for understanding associations between genomic variations (e.g., SNPs and CNVs) and clinical phenotypes, causal relationships between those variations and phenotypes, or functional pathways in response to evolutionary, environmental, and physiological changes, among others. MapReduce-style parallel processing can be used for improved performance. For example, alignment, quality score recalibration, and variation discovery algorithms can be parallelized using the open-source Hadoop system.

FIG. 4 shows an exemplary training data set. The training set comprises values for each of 1,000 different mixtures. Values for each mixture include class labels which may identify the presence of sequences in the mixture having named bases at particular base positions, and/or tally vectors for counts of bases at each base position in each mixture.

Instead of a high-volume DNA sequencer, the system can use a handheld DNA sequencer or a desktop DNA sequencer. The DNA sequencer can apply Gilbert's sequencing method based on chemical modification of DNA followed by cleavage at specific bases, or it can apply Sanger's technique which is based on dideoxynucleotide chain termination. The Sanger method became popular due to its increased efficiency and low radioactivity. The DNA sequencer can use techniques that do not require DNA amplification (polymerase chain reaction—PCR), which speeds up the sample preparation before sequencing and reduces errors. In addition, sequencing data is collected from the reactions caused by the addition of nucleotides in the complementary strand in real time. For example, the DNA sequencers can utilize a method called Single-molecule real-time (SMRT), where sequencing data is produced by light (captured by a camera) emitted when a nucleotide is added to the complementary strand by enzymes containing fluorescent dyes. Alternatively, the DNA sequencers can use electronic systems based on nanopore sensing technologies.

Data is sent by the DNA sequencers over a direct connection or over the internet to a computer for processing. The data processing aspects of the system can be implemented in digital electronic circuitry, or in computer hardware, firmware, software, or in combinations of them. The database 300 can also communicate with a cloud-based system such as Amazon's AWS system. One embodiment uses an elastic load balancer 410 communicating with an auto-scaling instance group. The group has a plurality of security group members 420 with an instance 430 and BBS storage 440. In case of digital sequence processing or deep genetic analyzing/processing overload, the load balancer 410 can automatically starts additional instances to handle the load.

The cloud system 400 can be used for backup and instant recovery of an entire data center to a virtual computing environment. The system can also provide backup and restoration of all data center components including, without limitation, physical machines, virtual machines, routers, networks, subnetworks, switches, firewall, directory lookup, DNS, DHCP, and internet access. In one implementation, a backup of the database 300 and supporting local computers can be created, and configuration information of each working computer may be saved together with each backup image, supplemental to the image. The configuration information includes persistent and volatile state. For example, each backup image is created as a snapshot of the corresponding computer. The snapshot comprises an application-consistent image as of a specific point in time of primary storage of the computer. Information representing the state of the network connections of the computer may be saved together with the configuration information saved with the backup image, and the backup image may be loaded as a cloud computing node. Storage facilities from the source data base 300 may be recreated using software-defined storage in a public or private cloud. Storage facilities may include an Internet Small Computer Systems Interface (i SC SI) storage, Fibre Channel (FC) storage, or Network Attached Storage (NAS). Storage in the cloud may include, for example, Amazon Simple Storage Service (S3), AWS Storage Gateway, or Amazon Elastic Block Store (BBS).

In some embodiments, a metadata collection agent collects information regarding the components in a data center. In some embodiments, the metadata collection agent is resident on each device of the data center. In other embodiments, the metadata collection agent is resident on a node operatively connected to the data center via a computer network, and operable to collect metadata regarding each device of the data center. In some embodiments, those components of a data center having computer readable storage are automatically backed up to computer readable backup media. Computer readable backup media may include hard disk drives (HDD), solid-state drives (SSD), tape, compact disk (CD), digital video (or versatile) disk (DVD), Flash, diskette, EPROM, or other optical or magnetic storage media known in the art. In some embodiments, all information gathered during the backup process is sent to a selected destination.

In some embodiments, the information is sent to a destination by transport of a computer readable backup medium. In other embodiments, the information is replicated via a computer network to a disaster recovery (DR) site or to a public cloud.

Information regarding each physical and virtual machine in the data center is collected. Such information may vary based on the type of device in question, and may include: network configuration; disk volumes; application state; and operating system state. Network configuration information may include MAC addresses, IP addresses, open ports, and network topology. Disk volume information may include capacity, logical layout, partition maps, metadata regarding contents, as well as physical characteristics.

In some embodiments, the collection of information may include determining what components are required for each virtual or physical machine in the data center to operate. Examples of required components include: Network routers; Network firewalls; Internet Access; Directory Lookup (e.g., AD, LDAP), Single Sign-On, DHCP, DNS; iSCSI storage devices; FC storage devices; and NAS file servers (e.g., NFS or CIFS). Determining the required components may include collecting application specific information for each machine in the data center, and determining application dependencies of each application. Determining required components may also include analyzing network topology information to determine connected or accessible devices.

The collected information and the backup data may be used to recreate the source physical or virtual data center in a substitute data center. In some embodiments, the substitute data center may be software-defined to emulate the source data center. In some embodiments, the substitute data center comprises a plurality of physical machines that are dynamically reconfigured to conform to the source data center configuration. In other embodiments, the substitute data center may comprise a plurality of virtual machines that are dynamically configured to conform to the source data center configuration. In yet other embodiments, the substitute data center may comprise a plurality of cloud resources. The substitute data center may emulate, or provide the functional equivalent of, the source data center. In some embodiments, the substitute data center may provide a complete substitute for the source data center. In other embodiments, the substitute data center may provide only a selected subset of functionality of the source data center. For example, where a source data center has computation, network, and storage aspects, a subset of this functionality may be selected to be performed by the substitute data center. In some embodiments, multiple substitute data centers may each substitute for aspects of the source data center.

The system can establish communications directly with a medical practice/healthcare provider (treating professional) and/or a patient/subject through communication links. The system can also receive information from other labs such as medical laboratory, diagnostic laboratory, medical facility, medical practice, point-of-care testing device, or any other remote data site capable of generating subject clinical information. Subject clinical information includes, but it is not limited to, laboratory test data, X-ray data, examination, and diagnosis. The healthcare provider or practice may include medical services providers, such as doctors, nurses, home health aides, technicians and physician assistants, and the practice may be any medical care facility staffed with healthcare providers. In certain instances, the healthcare provider/practice may also be a remote data site. In a cancer treatment embodiment, the subject may be afflicted with cancer, among others.

Other clinical information for a cancer subject may include the results of laboratory tests, imaging or medical procedure directed towards the specific cancer that one of ordinary skill in the art can readily identify. The list of appropriate sources of clinical information for cancer may include, but is not limited to: CT scan, MM scan, ultrasound scan, bone scan, PET Scan, bone marrow test, barium X-ray, endoscopy, lymphangiogram, IVU (Intravenous urogram) or IVP (IV pyelogram), lumbar puncture, cystoscopy, immunological tests (anti-maligning antibody screen), and cancer marker tests.

The subject's clinical information may be obtained from the lab manually or automatically. For simplicity of the system, the information is obtained automatically at predetermined or regular time intervals. A regular time interval refers to a time interval at which the collection of the laboratory data is carried out automatically by the methods and systems described herein based on a measurement of time such as hours, days, weeks, months, years, etc. In an embodiment of the invention, the collection of data and processing may be carried out at least once a day. In another embodiment, the transfer and collection of data may be carried out once every month, biweekly, or once a week, or once every couple of days.

Alternatively, the retrieval of information may be carried out at predetermined but not regular time intervals. For instance, a first retrieval step may occur after one week, and a second retrieval step may occur after one month. The transfer and collection of data can be customized according to the nature of the disorder that is being managed and the frequency of required testing and medical examinations of the subjects.

The computer system can include a set of instructions that can be executed to cause the computer system to perform any one or more of the methods or computer-based functions disclosed herein. For example, the computer system may include instructions that are executable to perform the methods discussed with respect to FIGS. 1, 2A, and 2B. In particular embodiments, the computer system may include instructions to implement the application of a training algorithm to train an artificial-neural network or implement operating an artificial-neural-network in a feed-forward manner. In particular embodiments, the computer system may operate in conjunction with other hardware that is designed to perform methods discussed above. The computer system may be connected to other computer systems or peripheral devices via a network. Additionally, the computer system may include or be included within other computing devices. The computer system may include a processor, e.g., a central processing unit (CPU), a graphics processing unit (GPU), or both. Moreover, the computer system can include a main memory and a static memory that can communicate with each other via a bus. As shown, the computer system may further include a video display unit, such as a liquid crystal display (LCD), a projection television display, a flat panel display, a plasma display, or a solid state display. Additionally, the computer system may include an input device, such as a remote control device having a wireless keypad, a keyboard, a microphone coupled to a speech recognition engine, a camera such as a video camera or still camera, or a cursor control device, such as a mouse device. The computer system can also include a disk drive unit, a signal generation device, such as a speaker, and a network interface device. The network interface enables the computer system to communicate with other systems via a network. In a particular embodiment the disk drive unit may include a non-transitory computer-readable medium in which one or more sets of instructions, e.g., software, can be embedded. For example, instructions for applying a training algorithm to an artificial-neural-network or instructions for operating an artificial neural-network in a feed-forward manner can be embedded in the computer-readable medium.

Further, the instructions may embody one or more of the methods or logic as described herein. In a particular embodiment, the instructions may reside completely, or at least partially, within the main memory, the static memory, and/or within the processor during execution by the computer system. The main memory and the processor also may include computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations, or combinations thereof.

While the computer-readable medium is shown to be a single medium, the term "computer readable medium" includes a single medium or multiple media, such as a centralized or distributed database, and/or associated caches and servers that store one or more sets of instructions. The term "computer-readable medium" shall also include any medium that is capable of storing or encoding a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more nonvolatile read-only memories. Further, the computer-readable medium can be a random access memory (RAM) or other volatile re-writable memory. Additionally, the computer-readable medium can include a magneto-optical or optical medium, such as a disk or tapes or other storage device to capture carrier wave signals, such as a signal communicated over a transmission medium. Accordingly, the disclosure is considered to include any one or more of a computer-readable medium or other equivalents and successor media, in which data or instructions may be stored.

It will be apparent from the foregoing embodiments that many other modifications, variants, and embodiments are possible. For example, although the above described embodiments use computers or digital signal processing devices to emulate a plurality of neuron units, in another embodiment of the invention, the network is implemented by a custom VLSI circuit comprising a rectangular array of neurons on a substrate, each neuron unit comprising the structures described in relation to FIG. 6. This embodiment is suitable for very high speed operation, since calculations of all neurons in a given layer are performed in parallel, so that the total processing time required to execute the neural network scales with the number of layers, rather than with the total number of neurons as in the embodiments described above. In another embodiment, the neural network is implemented as a sampled analogue circuit, using analogue shift register devices (such as charge coupled devices (CCDs) or bucket brigade devices (BBDs)) as the serial to parallel converters, analogue multipliers and accumulators, and an analogue function generator for the non-linear function. Multiplying digital to analogue converters could be used as the weight multipliers, using the downloaded digital weight values to generate an analogue signal to an analogue input.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for detecting a presence or an absence of a tumor-derived somatic single-nucleotide variation (SNV) in a cell-free deoxyribonucleic acid (DNA) sample of a human subject having a cancer, comprising:
    (a) obtaining the cell-free DNA sample from the human subject having the cancer;
    (b) sequencing a plurality of tumor-derived cell-free DNA molecules from the cell-free DNA sample to produce a set of tumor-derived cell-free DNA sequence reads;
    (c) mapping a plurality of the set of tumor-derived cell-free DNA sequence reads to a reference sequence to produce a set of mapped sequence reads;
    (d) applying a trained machine learning classifier to the set of mapped sequence reads to generate outputs that correspond to individual probabilities of adenine (A), cytosine (C), guanine (G), and thymine (T) being present at individual genomic positions of a plurality of genomic base positions among the set of mapped sequence reads;
    (e) determining, by the trained machine learning classifier and based on the individual probabilities for a genomic base position of the plurality of genomic base positions, one or more base calls at the genomic base position for individual mapped sequence reads of the set of mapped sequence reads, wherein:
        the one or more base calls indicate a presence of at least one of A, C, G, or T at the genomic base position in one or more tumor-derived cell-free DNA molecules,
        the genomic base position corresponds to the tumor-derived somatic SNV, and
        the trained machine learning classifier is trained by:
            (i) generating training data with class labels, wherein the training data comprises a plurality of mapped sequence reads generated from a plurality of training cell-free DNA samples comprising tumor-derived cell-free DNA molecules from human subjects having cancer;
            (ii) in computer memory, constructing the machine learning classifier configured to:
                receive input features extracted from the plurality of mapped sequence reads of the plurality of training cell-free DNA samples, and
                generate outputs for each of adenine (A), cytosine (C), guanine (G), and thymine (T) base calls based on the input features; and
            (iii) training the machine learning classifier with the training data;
    (f) determining a number or a frequency of mapped sequence reads from among the set of mapped sequence reads having one or more variant base calls at the genomic base position that differ from the reference sequence; and
    (g) detecting the presence or the absence of the tumor-derived somatic SNV in the cell-free DNA sample of the human subject having the cancer, based at least in part on the number or the frequency of the mapped sequencing reads determined in (f).

2. The method of claim 1, wherein the cell-free DNA sample is obtained or derived from a blood sample of the human subject.

3. The method of claim 1, wherein (d) further comprises determining a confidence level for the plurality of one or more base calls.

4. The method of claim 1, wherein the input features comprise tally, vectors comprising:
    (1) counts of each of adenine (A), cytosine (C), guanine (G), and thymine (T) at a genomic base position of interest of a given sequence read from the plurality of sequence reads of the training data; or
    (2) sub-count components of (i).

5. The method of claim 4, wherein the tally vectors comprise (1) and (2).

6. The method of claim 1, wherein the input features comprise statistics of a plurality of base calls performed at the genomic base position on a plurality of mapped sequence reads generated from a plurality of reference cell-free DNA samples comprising cell-free DNA molecules from reference human subjects not having cancer.

7. The method of claim 1, wherein the tumor-derived somatic SNV comprises an allele frequency that is less than or equal to about 1%.

8. The method of claim 7, wherein the tumor-derived somatic SNV comprises an allele frequency that is less than or equal to about 0.1%.

9. The method of claim 1, wherein (f) comprises determining the number of the mapped sequence reads from among the set of mapped sequence reads having the one or more variant base calls from the plurality of base calls at the genomic base position that differ from the reference sequence, and wherein (g) comprises detecting the presence or the absence of the tumor-derived somatic SNV in the cell-free DNA sample of the human subject having the cancer, based on the number of the mapped sequencing reads determined in (f).

10. The method of claim 1, wherein (f) comprises determining the frequency of the mapped sequence reads from among the set of mapped sequence reads having the one or more variant base calls from among the plurality of base calls at the genomic base position that differ from the reference sequence, and wherein (g) comprises detecting the presence or the absence of the tumor-derived somatic SNV in the cell-free DNA sample of the human subject having the cancer, based on the frequency of the mapped sequencing reads determined in (f).

11. The method of claim 1, further comprising determining a second number or a second frequency of mapped sequence reads from among the set of mapped sequence reads having one or more non-variant base calls from among the plurality of base calls at the genomic base position that match the reference sequence, and wherein (g) comprises detecting the presence or the absence of the tumor-derived somatic SNV in the cell-free DNA sample of the human subject having the cancer, based at least in part on the second number or the second frequency of the mapped sequence reads.

12. The method of claim 1, wherein the reference sequence is at least a portion of a human reference genome.

13. The method of claim 12, wherein the reference sequence is the human reference genome.

14. The method of claim 1, wherein the trained machine learning classifier comprises a statistical model or a Bayesian model.

15. The method of claim 1, wherein (d) comprises discarding a subset of the set of mapped sequence reads based on a call score of a base position among the set of mapped sequence reads.

16. The method of claim 1, wherein the trained machine learning classifier comprises a neural network or a support vector machine, and wherein training the machine learning classifier comprises adjusting a set of weights of the neural network or the support vector machine.

17. The method of claim 1, wherein the trained machine learning classifier comprises an output layer having a plurality of nodes with individual nodes of the plurality of nodes corresponding to one of adenine (A), cytosine (C), guanine (G), or thymine (T) and output of the individual nodes comprises the individual probabilities of adenine (A), cytosine (C), guanine (G), or thymine (T) being present at one or more genetic positions.

18. The method of claim 1, wherein the class labels indicate an identity of variants at one or more base positions.

19. A system for detecting a presence or an absence of a tumor-derived somatic single-nucleotide variation (SNV) in a cell-free deoxyribonucleic acid (DNA) sample of a human subject having a cancer, comprising:
  computer memory comprising a trained machine learning classifier, wherein the trained machine learning classifier is trained by:
    (i) generating training data with class labels, wherein the training data comprises a plurality of mapped sequence reads generated from a plurality of training cell-free DNA samples comprising tumor-derived cell-free DNA molecules from human subjects having cancer;
    (ii) in computer memory, constructing the machine learning classifier configured to receive input features extracted from the plurality of mapped sequence reads of the plurality of training cell-free DNA samples and generate outputs for each of adenine (A), cytosine (C), guanine (C), and thymine (T) base calls based on the input features; and
    (iii) training the machine learning classifier with the training data; and one or more computer processors that are individually or collectively programmed to:
  (a) obtain sequence data derived from a plurality of tumor-derived cell-free DNA molecules from a cell-free DNA sample obtained from the human subject having the cancer, the sequence data including a set of tumor-derived cell-free DNA sequence reads;
  (b) map a plurality of the set of tumor-derived cell-free DNA sequence reads to a reference sequence to produce a set of mapped sequence reads;
  (c) apply the trained machine learning classifier to the set of mapped sequence reads to generate outputs that correspond to individual probabilities of adenine (A), cytosine (C), guanine (G), and thymine (T) being present at individual genomic positions of a plurality of genomic base positions among the set of mapped sequence reads;
  (d) determining, by the trained machine learning classifier and based on the individual probabilities for a genomic base position of the plurality of genomic base positions, one or more base calls at the genomic base position wherein the one or more base calls indicate a presence of at least one of A, C, G, or T at the genomic base position in one or more tumor-derived cell-free DNA molecules and the genomic base position corresponds to the tumor-derived somatic SNV;
  (e) determine a number or a frequency of mapped sequence reads from among the set of mapped sequence reads having one or more variant base calls from among the plurality of base calls at the genomic base position that differ from the reference sequence; and
  (f) detect the presence or the absence of the tumor-derived somatic SNV in the cell-free DNA sample of the human subject having the cancer, based at least in part on the number or the frequency of the mapped sequencing reads determined in (e).

20. A non-transitory computer-readable medium comprising machine executable code that, upon execution by one or more computer processors, implements a method for detecting a presence or an absence of a tumor-derived somatic single-nucleotide variation (SNV) in a cell-free deoxyribonucleic acid (DNA) sample of a human subject having a cancer, the method comprising:
  (a) obtaining sequence data derived from a plurality of tumor-derived cell-free DNA molecules from a cell-free DNA sample obtained from the human subject having the cancer, the sequence data comprising a set of tumor-derived cell-free DNA sequence reads;
  (b) mapping a plurality of the set of tumor-derived cell-free DNA sequence reads to a reference sequence to produce a set of mapped sequence reads;
  (c) applying a trained machine learning classifier to the set of mapped sequence reads to generate outputs that correspond to individual probabilities of adenine (A), cytosine (C), guanine (G), and thymine (T) being present at individual genomic positions of a plurality of genomic base positions among the set of mapped sequence reads;
  (d) determining, by the trained machine learning classifier and based on the individual probabilities for a genomic base position of the plurality of genomic base positions, one or more base calls at the genomic base position, wherein:

the one or more base calls indicate a presence of at least one of A, C, G, or T at the genomic base position in one or more tumor-derived cell-free DNA molecules, the genomic base position corresponds to the tumor-derived somatic SNV, and the trained machine learning classifier is trained by:
(i) generating training data with class labels, wherein the training data comprises a plurality of mapped sequence reads generated from a plurality of training cell-free DNA samples comprising tumor-derived cell-free DNA molecules from human subjects having cancer;
(ii) constructing the machine learning classifier configured to receive input features extracted from the plurality of mapped sequence reads of the plurality of training cell-free DNA samples and generate outputs for each of adenine (A), cytosine (C), guanine (G), and thymine (T) base calls based on the input features; and
(iii) training the machine learning classifier with the training data;

(e) determining a number or a frequency of mapped sequence reads from among the set of mapped sequence reads having one or more variant base calls from among the plurality of base calls at the genomic base position that differ from the reference sequence; and (f) detecting the presence or the absence of the tumor-derived somatic SNV in the cell-free DNA sample of the human subject having the cancer, based at least in part on the number or the frequency of the mapped sequencing reads determined in (e).

* * * * *

UNITED STATES PATENT AND TRADEMARK OFFICE
CERTIFICATE OF CORRECTION

PATENT NO. : 11,527,305 B2
APPLICATION NO. : 17/178102
DATED : December 13, 2022
INVENTOR(S) : Bahram Ghaffarzadeh Kermani et al.

Page 1 of 1

It is certified that error appears in the above-identified patent and that said Letters Patent is hereby corrected as shown below:

In the Claims

Column 16, Line 38-39, Claim 3:
Remove "for the plurality of one or more" and replace it with --for the one or more--

Signed and Sealed this
Twenty-fifth Day of July, 2023

Katherine Kelly Vidal
*Director of the United States Patent and Trademark Office*